US00PP10899P

United States Patent [19]

Zaiger et al.

[11] Patent Number: Plant 10,899

[45] Date of Patent: May 18, 1999

[54] INTERSPECIFIC TREE 'FLAVOR ANN'

[75] Inventors: Chris Floyd Zaiger; Gary Neil Zaiger; Leith Marie Gardner; Grant Gene Zaiger, all of Modesto, Calif.

[73] Assignee: Guillou Freres J.B. Et M., St. Malo, France

[21] Appl. No.: 08/963,024

[22] Filed: Nov. 3, 1997

[51] Int. Cl.[6] ..... A01H 5/00

[52] U.S. Cl. ..... Plt./180

[58] Field of Search ..... Plt./39, 38.1, 33.1, Plt./180, 184, 186

*Primary Examiner*—Howard J. Locker
*Assistant Examiner*—Ann Marie Grünberg
*Attorney, Agent, or Firm*—Foley & Lardner

[57] ABSTRACT

A new and distinct variety of interspecific tree [ (*Prunus armeniaca*× (*Prunus salicina*×*Prunus armeniaca*)×*Prunus salicina*] which has the unique combination of desirable features that are outstanding in a new variety. The following features of the tree and its fruit were characterized with the tree budded on nemaguard rootstock, grown on Hanford sandy loam soil, Storie Index rating 95, in USDA hardiness zone 9, near Modesto, Calif., and with standard commercial cultural fruit growing practices, such as, pruning, thinning, spraying, irrigation, fertilization, etc.:

1. Early maturity of the fruit.
2. Fruit with good flavor and eating quality.
3. Regular and heavy production of fruit.
4. Fruit with good handling and shipping quality.
5. Having the ability to adequately pollinate Flavorella PlumCot (U.S. Plant Pat. No. 8,470).
6. Vigorous, semi-spreading growth.

1 Drawing Sheet

ORIGIN OF THE VARIETY

The present new and distinct variety of interspecific tree [(Apricot×PlumCot)×Plum] was originated by us in our experimental orchard located near Modesto, Calif., as a first generation cross between a selected seedling with field identification number 87EB90 with Royal Zee Plum (U.S. Plant Pat. No. 5,486). The maternal parent (87EB90) originated as a selected seedling from a cross of an apricot seedling selection (15W297) with the plumcot seedling selection (4G1180). The Selection (15W297) originated from open pollinated Flaming Gold Apricot (U.S. Plant Pat. No. 2,822) seed. The plumcot selection (4G1180) originated from an open pollinated Red Beaut Plum (U.S. Plant Pat. No. 2,539) seed. A large group of these first generation crosses growing on their own root were planted and maintained under close observation by us, during which time, one such seedling which is of the present variety, being especially desirable for its fruit characteristics and its ability to pollinate Flavorella PlumCot (U.S. Plant Pat. No. 8,470), was selected for asexual propagation and commercialization.

ASEXUAL REPRODUCTION OF THE VARIETY

Asexual reproduction of the new and distinct variety of interspecific tree was by budding to nemaguard rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

A new and distinct variety of interspecific tree [ (Apricot× PlumCot)×Plum] which is of large size, vigorous, semi-spreading growth and a productive and regular bearer of yellow flesh, freestone fruit with good flavor and eating quality. The fruit is further characterized by having firm flesh, good handling and shipping quality and being relatively uniform in size throughout the tree. The present variety of interspecific tree grows similar to an apricot tree, has a slightly rougher bark condition, produces flowers that are similar in size and shape of an apricot but lighter in color. The bloom time coincides with Flavorella PlumCot (U.S. Plant Pat. No. 8,470) and the pollen is abundant, self-fertile and pollinates Flavorella.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in it suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large — tree growth pruned to 12' to 14' in height and 12' to 14' in width for economical harvesting of fruit.

*Vigor.*—Vigorous — growing to 6 to 8 feet in height and 5 to 7 feet in width the first growing season. Pruned in the late fall or early winter to select desirable scaffolds.

*Form.*—Semi-spreading, growth habit similar to normal apricot tree (heavy crop load has tendency to spread tree width).

*Productivity.*—Productive — fruit set varies with climatic conditions during blooming period. Five consecutive years of adequate fruit set.

*Bearer.*—Regular. Fruit thinning varied from ¼ to ½ of crop load over a 5 year period.

*Density.*—Dense. Foliage from numerous smaller (¼" to ¾" caliper) branches growing throughout the tree, create this dense condition. Normal apricot pruning to a vase shape allows for more sunlight and air movement throughout the center of the tree, which enhances fruit color, Brix and productivity.

Trunk:

*Size.*—Medium to large.

*Texture.*—Medium shaggy.

*Color.*—Brown to soot brown (5-E-5) to (5-F-5).

Branches:

*Size.*—Medium.

*Texture.*—Smooth to medium rough, varies with age of growth.

*Lenticels.*—Numerous. Large size.

*Color.*—Light brown to hair brown (5-D-6) to (5-E-4).

Leaves:

*Size.*—Large. Average length 4". Average width 2½".

*Form.*—Obovate.

*Margin.*—Serrate.

*Thickness.*—Medium.

*Surface.*—Smooth.

*Petiole.*—Average length 1⅛". Medium width.

*Glands.*—Globose. Number varies from 0 to 4. Average number 2. Small size. Located on petiole.

*Color.*—Upper surface — green to dark green (28-F-5) to (28-F-7). Lower surface — grayish green to cactus green (28E-4) to (28-E-6).

Flower buds:

*Size.*—Medium.

*Length.*—Medium.

*Form.*—Plump.

*Pubescence.*—Pubescent.

Flowers:

*Size.*—Large. 1⅛" to 1¼" in diameter.

*Pollen.*—Present, self-fertile. Pistil extends slightly above anthers.

*Blooming period.*—Date of first bloom: Feb. 13, 1996. Date of full bloom: Feb. 19, 1996. Varies slightly with climatic conditions.

*Color.*—Pale pink (7-A-2) to (8-A-2), color fades with age of bloom.

Fruit:

*Maturity when described.*—Firm ripe.

*Date of first picking.*—May 13, 1996.

*Date of last picking.*—May 18, 1996. Varies slightly with climatic conditions.

*Size.*—Average diameter axially 2⅜". Transverse diameter in suture plane 2". Diameter measured at right angles to suture plane 1⅞". Average weight 70 grams. Varies from 65 grams to 76 grams.

*Juice.*—Moderate amount, good balance between acid and sugar. enhances eating quality of fruit. Brix range 14.7 to 18.8, average 16. The Brix varies slightly with climatic conditions, warm sunny conditions during fruit maturity increases Brix.

*Form.*—Nearly globose, sides slightly flattened toward suture plane.

*Suture.*—Pronounced, extends from base to apex.

*Ventral surface.*—Lipped, approximately 1/16".

*Apex.*—Varies from rounded to slightly retuse.

*Base.*—Retuse.

*Cavity.*—Rounded to slightly elongated in suture plane. Average depth ⅛". Average breadth ½".

Stem:

*Size.*—Varies from ⅛" to 5/32" in length, average diameter 3/32", enlarged at fruit attachment.

*Color.*—Varies from dull green to grayish green (28-D-5) to (28-D-7).

Flesh:

*Ripens.*—Evenly.

*Texture.*—Firm.

*Fibers.*—Few, small tender.

*Aroma.*—Slight.

*Amygdalin.*—Wanting.

*Eating quality.*—Good.

*Flavor.*—Good.

*Color.*—Varies from yellowish white (4-A-2) near pit cavity to maize yellow (4-A-6) near skin surface. Pit cavity varies from maize yelow to grayish yellow (4-A-6).

Skin:

*Thickness.*—Medium.

*Texture.*—Medium, tenacious to flesh.

*Down.*—Abundant, very short.

*Tendency to crack.*—None.

*Color.*—Sunflower yellow to golden yellow (4-A-7) to (5-A-7). Color varies during maturity stage, changing from green, to straw color and at maturity becomes sunflower yellow to golden yellow. Fruit exposed to sunlight have a greater percentage of golden yellow color than fruit shaded by leaves. Color also varies with climatic conditions, cloudy and rainy conditions during the fruit maturity stage reduces the percentage of golden yellow color.

Stone:

*Type.*—Freestone.

*Size.*—Medium. Average length 1⅛". Average width ⅞". Average thickness 7/16".

*Form.*—Varies from ovoid to obovoid.

*Base.*—Usually straight, varies from straight to rounded.

*Apex.*—Nearly rounded, varies from round to acuminate.

*Surface.*—Lightly pitted throughout with shallow grooves extending from base to apex on each side of suture plane.

*Sides.*—Varies from equal to unequal. Some stones are unequal with one side being slightly larger in size. Stone size and shape may vary slightly with cliatic conditions. Wet weather during bloom time can result in a percentage of fruit without viable embryos, shattered or misshapen stones.

*Tendency to split.*—None.

*Color.*—Light brown and brown (5-C-5) to (5-D-5).

Use: Pollinator for Flavorella PlumCot (U.S. Plant Pat. No. 8,470). Dessert. Market, local and long distance.

Keeping quality: Good. The fruit holds firm on the tree for 6 to 7 days after maturity (shipping ripe).

Shipping quality: Good. The firm flesh of the fruit revealed minimal flesh bruising or skin scaring during packing and shipping trials.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, semi-spreading growth and a productive and regular bearer of large, firm, yellow flesh, freestone fruit with good handling and shipping quality; the fruit is further characterized by being relatively uniform in size throughout the tree, having good flavor and eating quality and the pollen from the flowers of the new variety being abundant, self-fertile and being a good pollinator for the PlumCot Flavorella (U.S. Plant Pat. No. 8,470).

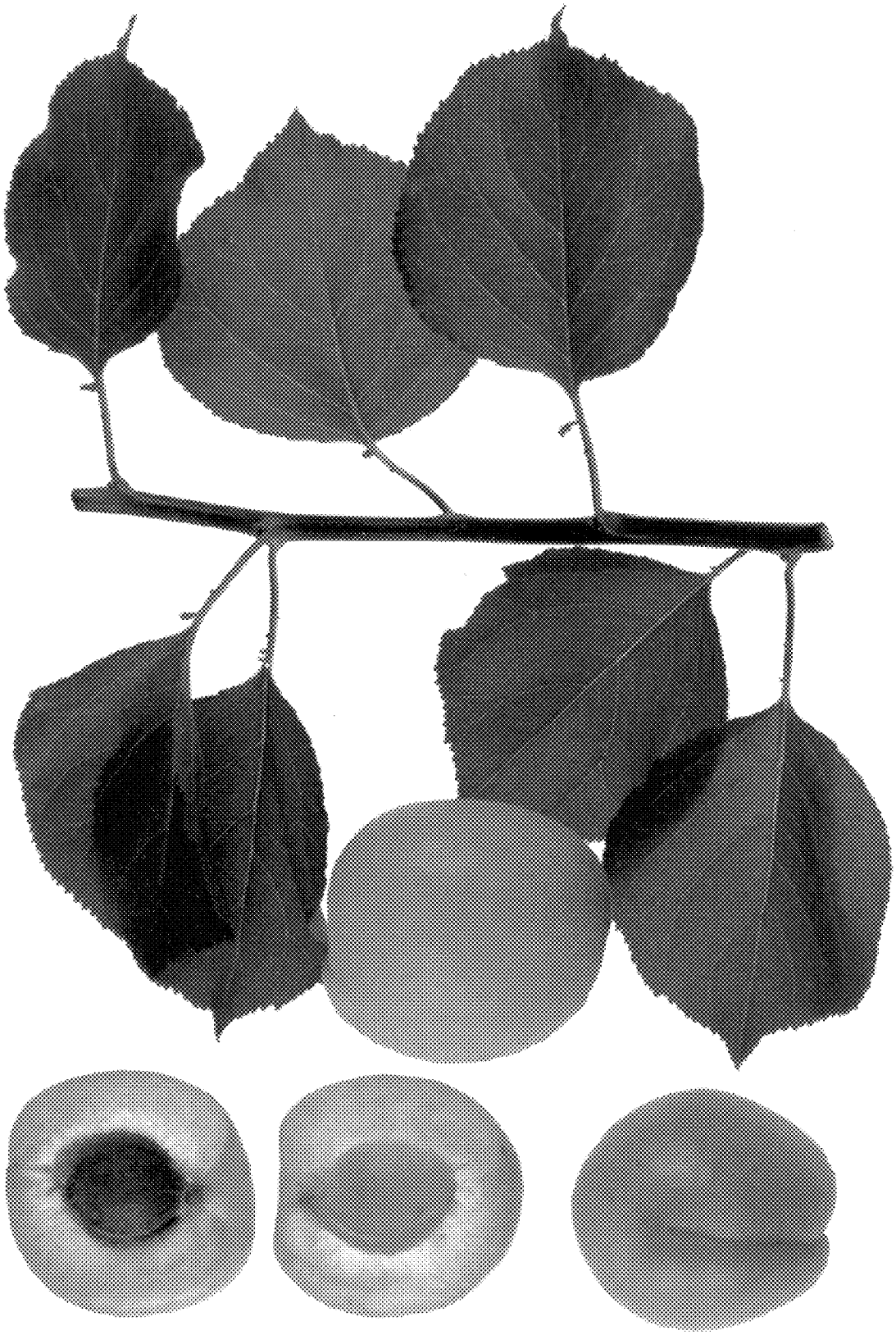

* * * * *